United States Patent [19]

Holan et al.

[11] 4,339,458
[45] Jul. 13, 1982

[54] INSECTICIDAL ESTERS

[75] Inventors: George Holan, Brighton; David F. O'Keefe, Mount Waverley, both of Australia

[73] Assignee: Commonwealth Scientific and Industrial Research Organization, Australia

[21] Appl. No.: 147,728

[22] Filed: May 8, 1980

Related U.S. Application Data

[62] Division of Ser. No. 969,862, Dec. 12, 1978, Pat. No. 4,235,926.

[30] Foreign Application Priority Data

Dec. 19, 1977 [AU] Australia .............................. PD2818

[51] Int. Cl.³ ............................................ A01N 43/16
[52] U.S. Cl. .................... 424/282; 549/435; 549/442; 549/447; 549/444
[58] Field of Search .................. 260/340.5 R; 424/282

[56] References Cited

U.S. PATENT DOCUMENTS

| | | | |
|---|---|---|---|
| 3,666,789 | 5/1972 | Itaya et al. | 260/340.5 R |
| 3,835,176 | 9/1974 | Matsuo et al. | 260/465 D |
| 3,968,137 | 7/1976 | Andreades et al. | 560/21 |
| 4,060,632 | 11/1977 | Addor | 424/308 |
| 4,130,656 | 12/1978 | Greuter et al. | 260/465 D |

OTHER PUBLICATIONS

Chem. Abstract, 88:152264u.

Primary Examiner—Ethel G. Love
Attorney, Agent, or Firm—Bacon & Thomas

[57] ABSTRACT

Compounds of the general formula I

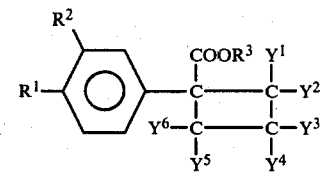

wherein $R^1$ is hydrogen or a methoxy, ethoxy, propoxy, butoxy, tetrafluoroethoxy, methylthio, ethylthio, propylthio, fluoro, chloro, bromo, methyl, ethyl, or nitro group, and $R^2$ is hydrogen or a methyl group, or $R^1$ and $R^2$ together form a methylenedioxy group;

$R^3$ is hydrogen, or a lower alkyl group, or one of the following groups (a) to (f):
(a) 3-phenoxybenzyl
(b) 2-benzyl-4-furylmethyl
(c) α-cyano-3-phenoxybenzyl
(d) 3,4-methylenedioxybenzyl
(e) α-ethynyl-3-phenoxybenzyl
(f) α-cyano-3-(4'-chlorophenoxy)-benzyl and $Y^1$, $Y^2$, $Y^3$, $Y^4$, $Y^5$ and $Y^6$ are the same or different groups and each is hydrogen or a fluoro, bromo or chloro group, with the proviso that when $R^1$ is hydrogen, fluoro, chloro, bromo or methyl and $R^2$ is hydrogen, then one of $Y^1$ to $Y^6$ is other than hydrogen.

The compounds in which $R^3$ is one of groups (a) to (f) are insecticides.

12 Claims, No Drawings

INSECTICIDAL ESTERS

This is a division, of application Ser. No. 969,862, filed Dec. 12, 1978, now U.S. Pat. No. 4,235,926.

This invention relates to new insecticidal compounds, methods of preparing these compounds and to new insecticidal compositions containing the compounds.

Throughout this specification, where the context permits, the word "insect" is used in its broad common usage and includes spiders, mites, nematodes and other pests which are not classed as insects in the strict biological sense. Thus the term implies reference not only to those small invertebrate animals belonging mostly to the class Insecta, comprising six-legged, usually winged forms, such as beetles, bugs, flies and the like, but also to other allied classes of arthropods whose members are wingless and usually have more than six legs, such as spiders, wood lice and the like, and especially to the order Acaridae which includes the mites and ticks. The words "insecticide" and "insecticidal" are similarly used.

The compounds provided by this invention have the general formula I

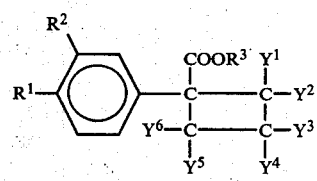

wherein $R^1$ is hydrogen or a methoxy, ethoxy, propoxy, butoxy, tetrafluoroethoxy, methylthio, ethylthio, propylthio, fluoro, chloro, bromo, methyl, ethyl, or nitro group, and $R^2$ is hydrogen or a methyl group, or $R^1$ and $R^2$ together form a methylenedioxy group;

$R^3$ is hydrogen, or a lower alkyl group, or one of the following groups (a) to (f):

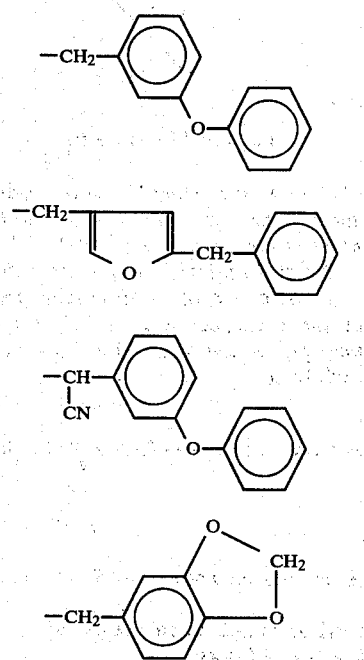

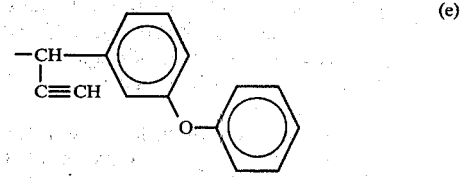

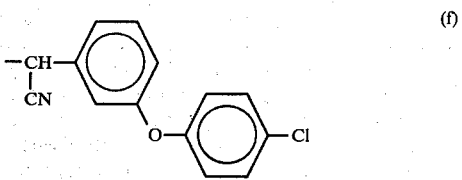

and $Y^1$, $Y^2$, $Y^3$, $Y^4$, $Y^5$ and $Y^6$ are the same or different groups and each is hydrogen or a fluoro, bromo or chloro group, with the proviso that when $R^1$ is hydrogen, fluoro, chloro, bromo or methyl and $R^2$ is hydrogen, then one of $Y^1$ to $Y^6$ is other than hydrogen.

Known compounds which can be regarded as related to the compounds of formula I are those in which the groups (a) to (f) are present as esterifying groups with chrysanthemic acid in commercial or experimental pyrethroids.

West German Patent Specification DT-OS 27 33 740 describes compounds of the formula I in which all of the groups $Y^1$ to $Y^6$ are hydrogen, $R^1$ and $R^2$ are each hydrogen, or a fluoro, chloro, bromo or methyl group and $R^3$ is one of the groups (a) (c) and (e) above. Such compounds are excluded from the present invention.

The acid of the present invention (formula I, $R^3 = H$) and its esters are novel.

Preferably, $R^1$ is methoxy, ethoxy or propoxy group and $R^2$ is hydrogen. Compounds in which $R^1$ and $R^2$ form the methylenedioxy group are also preferred.

Preferably also, $R^3$ is one of groups (a), (c) and (e) as defined above.

It is also preferred that from one to all six of the groups $Y^1$ to $Y^6$ is a fluoro group, the remainder (if any) being hydrogen. Tetrafluoro-substitution ($Y^1$, $Y^2$, $Y^3$, $Y^4 = F$; $Y^5$, $Y^6 = H$) is especially preferred.

Specifically preferred compounds in accordance with the invention are as follows:

3'-phenoxybenzyl 1-(3,4-methylenedioxyphenyl)-2,2,3,3-tetrafluorocyclobutanecarboxylate, and its α-cyano and α-ethynyl derivatives; 3'-phenoxybenzyl 1-(4-ethoxyphenyl)-2,2,3,3-tetrafluorocyclobutane carboxylate, and its α-cyano and α-ethynyl derivatives.

The compounds of formula I in which $R^3$ is one of groups (a) to (f) are extremely active as insecticides, having an insecticidal activity an order of magnitude greater than most known insecticides. These compounds also possess the property of contact repellency to insects. The compounds of the present invention are generally more active against flies than the compounds of our aforementioned copending application.

The compounds of formula I in which $R^3 = H$ or lower alkyl are useful as intermediates in the preparation of the other esters with $R^3 = $ (a) to (f) as shown below.

The compounds of formula I are optically active and can be resolved into their optical isomers by conventional methods. The invention thus includes the individual (+) and (−) optical isomers of the compounds as well as the racemic (±) forms.

It should also be noted that the insecticidal activities of the optical isomers of the compounds I with $R^3=$(a) to (f) may differ by an order of magnitude or more.

The invention also includes methods for the synthesis of the compounds I.

The compounds I in which R is one of the groups (a) to (f) may be prepared by esterification of the free acid (formula I, $R^3=H$) with the appropriate alcohol $R^3OH$, where $R^3$ is one of the groups (a) to (f). Such esterification may be carried out by any suitable known method, e.g., by direct reaction or by prior conversion of the acid and/or the alcohol to a suitable reactive derivative, or by an ester interchange reaction between the alcohol $R^3OH$ ($R^3=$(a) to (f) and a lower alkyl ester of the acid.

The acid (formula I, $R^3=H$) is prepared by the reaction of an appropriately substituted benzyl compound with an appropriately substituted 1,3-dihalopropane to form a 1-phenylcyclobutane compound which can be hydrolysed to the acid. This reaction scheme is as follows:

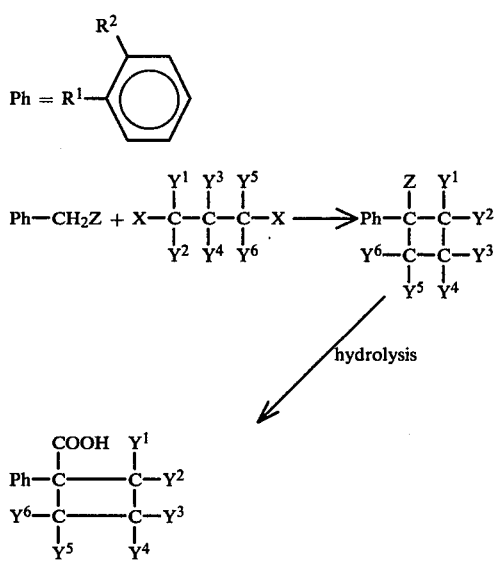

where Z represents a group which activates the benzylic methylene and is itself later hydrolysable to a carboxyl group, e.g., —C≡N or —COOEt; X represents a chloro, bromo or iodo group; $R^1$, $R^2$, $Y^1$, $Y^2$, $Y^3$, $Y^4$, $Y^5$ and $Y^6$ are as defined above.

An alternative method of preparation of the acid (formula I, $R^3=H$) as its lower alkyl ester is by addition of the olefin $Y^1Y^2C=CY^3Y^4$ to the substituted phenylacrylic ester of formula II

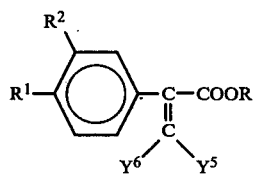

where R is a lower alkyl group and $R^1$, $R^2$, $Y^1$, $Y^2$, $Y^3$, $Y^4$, $Y^5$ and $Y^6$ are as defined above.

Esters of formula I ($R^3=$lower alkyl) wherein $Y^3=Y^4=F$ and $Y^1=Y^2=Y^5=Y^6=H$ can be made by first preparing the compounds wherein $Y^3=Y^4=F$, $Y^1=Y^2=Cl$ according to the preceding method (using dichlorodifluoroethylene) and then hydrogenating the product to replace the chlorine groups by hydrogen.

The esters II wherein $Y^5=Y^6=H$ may be obtained according to the following general procedure:

(1) A lower alkyl ester of the appropriately substituted phenylacetic acid (V) is condensed with a di(lower alkyl) oxalate in the presence of a basic catalyst, to produce an enolate salt (IV).

(2) The solution of the enolate salt is acidified to give the corresponding phenyloxaloacetate (III).

(3) The compound III is reacted with formaldehyde under alkaline conditions to give the phenyl hydroxymethyl acetate which on dehydration (sometimes spontaneously) yields the phenylacrylic ester (II).

This reaction sequence is illustrated in the following overall reaction scheme. It will be appreciated that the specific acids and bases indicated may be replaced by other suitable compounds. Also lower alkyl esters, other than the ethyl esters shown may be employed.

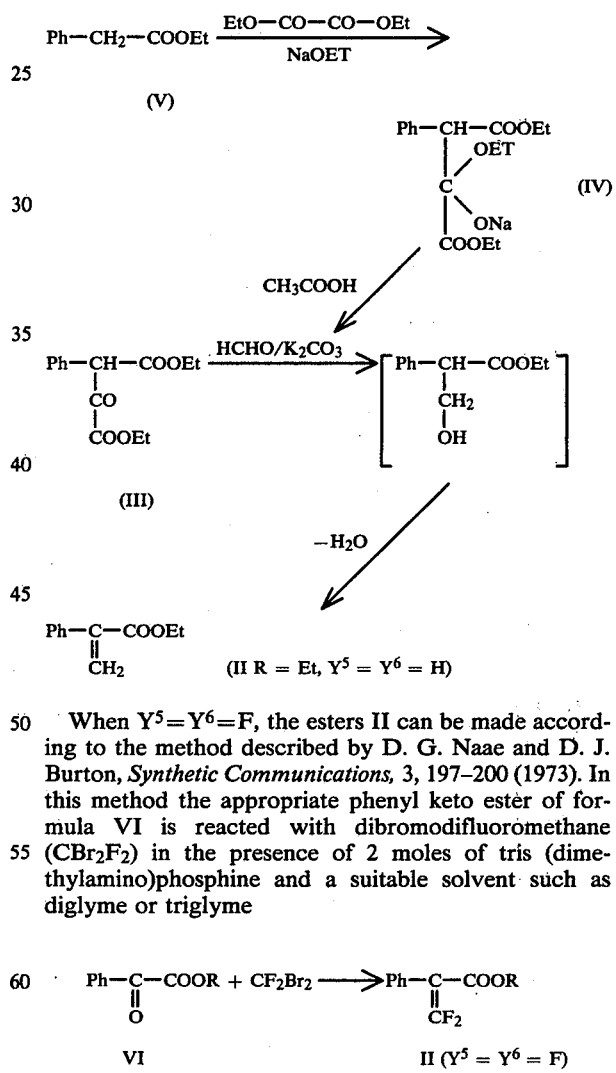

When $Y^5=Y^6=F$, the esters II can be made according to the method described by D. G. Naae and D. J. Burton, *Synthetic Communications*, 3, 197–200 (1973). In this method the appropriate phenyl keto ester of formula VI is reacted with dibromodifluoromethane ($CBr_2F_2$) in the presence of 2 moles of tris (dimethylamino)phosphine and a suitable solvent such as diglyme or triglyme

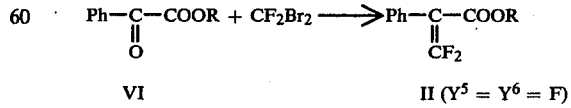

where Ph is as defined above and R is a lower alkyl group.

The general approach to formation of the esters of the invention is as follows:

$$A-COOEt \rightarrow A-COOH$$

$$A-COOH \rightarrow A-COCl$$

$$A-COCl + R^3OH \rightarrow A-COOR^3$$

where A is

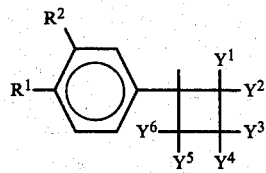

$R^1$, $R^2$, $Y^1$, $Y^2$, $Y^3$, $Y^4$, $Y^5$ and $Y^6$ are as defined above and $R^3$ is one of the groups (a) to (f) defined above.

Alternatively the ethyl ester can be directly converted as follows:

$$A-COOEt + R^3OH \rightarrow A-COOR^3 + EtOH$$

The new compounds described herein may be dissolved in a suitable organic solvent, or mixture of solvents, to form solutions or brought into aqueous suspension by dispersing organic solvent solutions of the compounds in water, to provide useful liquid compositions, which may be incorporated, for example, into aerosol-type dispersions with the usual propellants. The compounds may also be incorporated in solid compositions which may include inert solid diluents or carriers, to form useful solid compositions. Such compositions may also include other substances such as wetting, dispersing or sticking agents, and may be prepared in granular or other forms to provide slow release of the compounds over an extended period of time. The compounds may be employed in such compositions either as the sole toxic agent or in combination with other insecticides such as pyrethrum, rotenone, or with fungicidal or bactericidal agents, to provide compositions useful for household and agricultural dusts and sprays, textile coating and impregnation, and the like.

In particular, the compounds of the invention may be advantageously combined with other substances which have a synergistic or potentiating action. Generally such substances are of the class of microsomal oxidase inhibitors i.e., they inhibit the detoxification of insecticides in insects produced by the action of oxidative enzymes. Typical substances of this type are the pyrethrin synergists of which the following are examples:

| Common Name | Chemical Name |
|---|---|
| Piperonyl butoxide | α[2-(2-bytoxyethoxy)ethoxy]-4,5-methylenedioxy-2-propyl-toluene |
| Piperonyl cyclonene | 3-hexyl-5(3,4-methylenedioxy-phenyl)-2-cyclohexanone |
| "Sesoxane" (Sesamex) | 2-(3,4-methylenedioxy-phenoxy)-3,6,9-trioxaundecane |
| "Sulfoxide" | 1,2-(methylenedioxy)-4-[2-(octylsulfinyl)propyl]-benzene |
| n-Propyl isome | dipropyl-5,6,7,8-tetrahydro-7-methylnaphtho-[2,3-d]-1,3-dioxole-5,6-dicarboxylate |

("Sesoxane", "Sesamex" and "Sulphoxide" are Registered Trade Marks).

We have found that 'Sesoxane' (made by Shulton Inc., Clifton, N.J., U.S.A.) is particularly useful as a potentiator. The amount of 'Sesoxane' used may vary from 1/1000th to five times the weight of the compound I the preferred range being from about 1/100th to an equal part by weight. Piperonyl butoxide also is a useful potentiator in similar amounts.

The preparation and properties of the compounds of the invention are illustrated by the following specific examples. It should be noted, of course, that these examples are intended to be illustrative of the methods and procedures utilized in preparing the compounds and that they are not intended to be restrictive or to be regarded as embodying the only way in which the compounds can be formed and recovered.

EXAMPLE 1 (Prior Art Compound)

(a) 1-(4-chlorophenyl)cyclobutane nitrile

4-Chlorobenzyl cyanide (10 g) in dry DMSO (20 ml) was added over 5 min to a stirred suspension of sodium hydride (4.4 g) in DMSO at 25° C. under argon. The mixture was stirred for 30 minutes then a solution of 1,3-dibromopropane (27 g) in dry DMSO (50 ml) was added over 30 minutes while maintaining the temperature of the reaction mixture at 25°–30° C. After stirring an additional 40 minutes at this temperature the reaction mixture was added to ice water (500 ml) and extracted with dichloromethane (3×75 ml). The extracts were evaporated and the residue extracted with diethyl ether (4×50 ml). The ether extracts were washed with water, dried over anhydrous sodium sulphate and evaporated to yield an oil (10.8 g) which on distillation gave the nitrile [bp 90°/10$^{-6}$ Torr.] yield 5.4 g (43%).

Analysis: C 68.48% H 5.49% Cl 18.3%. $C_{11}H_{10}Cl\,N$ requires: C 68.93% H 5.26% Cl 18.5%.

(b) 1-(4-chlorophenyl)cyclobutane carboxylic acid 1-(4-chlorophenyl)cyclobutane nitrile (5 g) was mixed with ethylene glycol (60 ml) and 40% w/w aqueous potassium hydroxide solution (80 ml) and refluxed under argon for 18 hours. The mixture was cooled, added to ice water and extracted with diethyl ether. The aqueous layer was acidified and the precipitate was filtered off, washed with water, dried and recrystallised from petroleum ether (b.p. 40–60°) to give the acid as white needles mp 88°–9°, yield 4.5 g (82%).

Analysis: C 62.70% H 5.14% Cl 16.5% O 15.2%. $C_{11}H_{11}ClO_2$ requires: C 62.72% H 5.26% Cl 16.83% O 15.2%.

(c) 3'-phenoxybenzyl 1-(4-chlorophenyl)cyclobutane-carboxylate 1-(4-Chlorophenyl)cyclobutane carboxylic acid (1 g) was dissolved in thionyl chloride (1 ml) and heated at reflux for 40 minutes. Excess thionyl chloride was removed in vacuo and the residue was taken up in petroleum ether 40°–60° (40 ml) and added over 15 minutes to a stirred mixture of 3-phenoxybenzyl alcohol (1.1 g), pyridine (1 ml), benzene (50 ml) and petroleum ether 40°–60° (50 ml) maintained at 10° C. The mixture was stirred at 20°–25° C. for 3 hours then added to ice water, washed with 0.5 M hydrochloric acid, water, dilute sodium bicarbonate solution and dried over anhydrous sodium sulphate. The solvent was evaporated to give an oil (2.3 g) which after chromatography on silica gel, eluting with benzene/petroleum ether, gave the ester (1.52 g (82%).

Analysis: C 72.87% H 5.30% Cl 9.2% O 12.1% $C_{24}H_{21}ClO_3$ requires: C 73.37% H 5.39% Cl 9.0% O 12.2%.

EXAMPLE 2

(a) 1-(4-ethoxyphenyl)cyclobutane carboxylic acid

Ethyl 4-ethoxyphenylacetate (14 g) in anhydrous diethyl ether (20 ml) was added to a stirred suspension of sodamide (5.3 g) in liquid ammonia (400 ml) over 3 minutes and the mixture stirred for an additional 20 minutes. 1,3-dibromopropane (14 g) in diethyl ether (10 ml) was added over 20 minutes and the mixture stirred for 17 hours. 50 ml of saturated ammonium chloride solution was added and the reaction mixture extracted with diethyl ether. Evaporation of the solvent gave a residue (17.4 g) which after chromatography on silica gel by eluting with benzene/chloroform gave an oil (7.2 g). The oil was dissolved in ethanol (50 ml) and 10% sodium hydroxide solution (50 ml) was added. The mixture was refluxed for 3 hours, cooled, added to ice water and extracted with diethyl ether. The aqueous layer was acidified and the precipitate was filtered off, washed with water, dried and recrystallised from petroleum ether 40°–60° to give the acid 5.2 g (35%) mp 90°–1° C.

Analysis: C 71.04%, H 7.23% O 22.0% $C_{13}H_{16}O_3$ requires C 70.89% H 7.32% O 21.8%.

(b) 3'-phenoxybenzyl 1-(4-ethoxyphenyl)cyclobutane carboxylate 1-(4-ethoxyphenyl)cyclobutane carboxylic acid (1 g) was refluxed in thionyl chloride (1 ml) for 30 minutes and the excess thionyl chloride removed in vacuo. The residue was taken up in petroleum ether 40°–60° (25 ml) and added over 5 minutes to a stirred mixture of 3-phenoxybenzyl alcohol (1.1 g) pyridine (1 ml) benzene (25 ml) and petroleum ether 40°–60° (25 ml) at 15° C. The mixture was stirred at 15° C. for 3 hours, then added to ice water and extracted with diethyl ether. The extract was washed with water, 0.5 M hydrochloric acid, and sodium bicarbonate solution then dried over anhydrous sodium sulphate and the solvent removed to give an oil (2.1 g). Chromatography on silica gel, eluting with benzene, gave the ester 1.5 g (82%).

Analysis: C 77.55% H 6.65% O 16.0%. $C_{26}H_{26}O_4$ requires C 77.59% H 6.51% O 15.9%.

EXAMPLE 3

(a) 2-(4-ethoxyphenyl)propenoic acid ethyl ester.

This part of the example shows the general method of forming the 2-aryl-acrylic acid esters. (Formula II)

Alcohol-free sodium ethoxide freshly prepared from sodium (13.9 g) and excess ethanol was slurried in dry benzene (200 ml). To this suspension diethyl oxalate (88.5 g) was added over 15 minutes. Ethyl-p-ethoxyphenylacetate (V) (114.2 g) was added to the resulting clear yellow solution over 30 minutes at room temperature. After a further 1 hour period the reaction mixture solidified. The solid, sodium diethyl-2-p-ethoxyphenyl-3-ethoxy-3-oxido-oxaloacetate (IV) was triturated and washed well with ether. The combined ether washings were evaporated to a small volume to obtain a second crop of the salt.

The combined yield was 227.4 g.

The sodium salt was acidified by adding it in portions to a well stirred emulsion of equal parts of diethyl ether and dilute acetic acid (approximately 10%). After separation the ethyl layer was washed with water and dilute sodium bicarbonate solution, and dried with anhydrous sodium sulphate. After evaporation of the ether, the resulting oil was crystallized from petroleum ether (b.p. 60°–80°), to yield diethyl-2-p-ethoxyphenyloxaloacetate (III) 143.8 g (85%), m.p. 59°–60°.

The keto-ester III (143.8 g) was stirred in dilute formaldehyde solution (62 ml 37% formaldehyde+water 220 ml) and to the suspension potassium carbonate solution (54.5 g, in water 280 ml) was added dropwise. At the end of the addition, ether was added to the stirred suspension to dissolve the gummy precipitate which formed and after an additional 15 minutes, gas evolution commenced. When this gas evolution ceased (after about 2 hours) the reaction mixture was extracted with additional ether and the combined ether extracts were washed with water and evaporated after drying with $Na_2SO_4$. The yield of the ethyl 2-(4-ethoxyphenyl)propenoate (ii) (isolated as a yellow oil) was 97.8 g (79.8%).

(b) Ethyl 1-(4-ethoxyphenyl)-2,2,3,3-tetrafluorocyclobutane carboxylate 2-(4-ethoxyphenyl)propenoic acid ethyl ester (13.2 g) was mixed with benzene (7.5 ml), α-pinene (2 drops) N-ethyldiisopropyl amine (2 drops) and tetrafluoroethylene (15.5 ml) and heated to 150°–155° for 24 hours then 155°–60° C. for 17 hours. After evaporation of volatile materials the residue (16.6 g) was dissolved in dichloromethane and chromatographed on a column of silica gel to give the ester as a colourless oil 14.5 g (75%).

Analysis: C 56.47%, H 5.24%, F 23.4%. $C_{15}H_{16}F_4O_3$ requires C 56.25%, H 5.04%, F. 23.7%.

(c) 1-(4-ethoxyphenyl)-2,2,3,3-tetrafluorocyclobutane carboxylic acid

Ethyl 1-(4-ethoxyphenyl)-2,2,3,3-tetrafluorocyclobutane carboxylate (14.5 g) was dissolved in ethanol (100 ml) and a 10% w/w solution of sodium hydroxide in water (100 ml) was added and the mixture refluxed for 2.5 hours. The mixture was cooled, added to ice water and extracted with diethyl ether. The aqueous layer was acidified and the precipitate was filtered off, washed with water, dried and crystallised from 60°–80° petroleum ether to give the acid mp 112°–3° C. Yield 11.2 g (85%).

Analysis: C 53.20% H 4.22%, F 25.9%. $C_{13}H_{12}F_4O_3$ requires C 53.43% H 4.14% F 26.0%.

(d) 3'-phenoxybenzyl 1-(4-ethoxyphenyl)-2,2,3,3-tetrafluorocyclobutane-carboxylate 1-(4-ethoxyphenyl)-2,2,3,3-tetrafluorocyclobutane carboxylic acid (0.9 g) was refluxed with thionyl chloride (1 ml) for 45 minutes and the excess thionyl chloride was removed in vacuo. The residue was dissolved in petroleum ether 40°–60° (40 ml) and added over 5 minutes to a mixture of 3-phenoxybenzyl alcohol (1 g), pyridine (1 ml), benzene (25 ml), and petroleum ether 40°–60° (25 ml) maintained at 20° C. The mixture was stirred for 3 hours then added to ice water and extracted with diethyl ether. The extract was washed with water, 0.5 M hydrochloric acid, and sodium bicarbonate solution, dried over anhydrous sodium sulphate and the solvent evaporated to give an oil (2 g). Chromatography on silica gel by eluting with benzene gave the ester 1.2 g (82%).

Analysis: C 65.45%, H 4.84% F 16.0%. $C_{26}H_{22}F_4O_4$ requires C 65.82%, H 4.67%, F 16.0%.

EXAMPLE 4

(a) (−) Enantiomer of 1-(4-ethoxyphenyl)-2,2,3,3-tetrafluorocyclobutane carboxylic acid α(+)-(1-naphthyl)ethylamine was added to a solution of the racemic acid (2 g) (prepared as in Example 3(C)) in ethyl acetate (75 ml) and n-hexane. The salt which formed was crystallized four times from ethyl acetate at room temperature. The (+)(−) salt was decomposed with hydrochloric acid (1 M) and the residue recrystallized twice from ethanol. The (−) acid which had $\alpha_{20}{}^D = -118.2$ and m.p. 194° C. was obtained in 15% yield.

(b) (−) 3'-Phenoxybenzyl 1-(4-ethoxyphenyl)-2,2,3,3-tetrafluorocyclobutane carboxylate The resolved (−) acid, 0.2 g., was refluxed in thionylchloride (1 ml) for one hour. After evaporation of excess thionyl chloride, the residue was dissolved in petroleum ether (b.p. 60°-80°) and added to 3-phenoxybenzyl alcohol (0.139 g) and pyridine (0.238 g) in benzene (3 ml) and petroleum ether (3 ml). The reaction mixture was stirred overnight, quenched with ice-water, washed with water and the solvent layer separated and dried over molecular sieve. After evaporation of the solvent the pure ester was obtained as a viscous liquid by chromatography in silica gel using methylene chloride as the eluent. Yield 99.1%, $\alpha_{20}{}^D = -58.2$.

EXAMPLE 5

(a) 1-(3,4-methylenedioxyphenyl)-2,2,3,3-tetrafluorocyclobutane carboxylic acid A mixture of ethyl 2-(3,4-methylene dioxyphenyl) propenoate (2.2 g), tetrafluoroethylene (5 ml.), α-pinene (1 drop), N-ethyldiisopropylamine (1 drop) and benzene (10 ml), was heated at 150°-155° C. for 24 hours then at 160°-165° C. for 16 hours, then cooled. The solvent was evaporated to leave an oil (3.0 g). This oil was purified by chromatography on silica gel using benzene as eluent to give 1.4 g (44%) of ethyl 1-(3,4-methylene dioxyphenyl)-2,2,3,3-tetrafluorocyclobutane carboxylate.

The ethyl ester was hydrolysed by refluxing for 2 hours with a mixture of potassium hydroxide (5 g), water (50 ml) and ethanol (50 ml). The ethanol was removed by evaporation and the aqueous residue extracted with diethyl ether. The aqueous layer was acidified and the precipitate filtered off, dried and recrystallized from petroleum spirit (b.p. 60°-80°)/diethyl ether to yield 0.9 g of the acid as white crystals m.p. 168°-9° C.

Analysis: C 49.62%, H 2.72%, F 25.8%. $C_{12}H_8F_4O_4$ requires C 49.33%, H 2.76%, F 26.0%.

(b) 3'phenoxybenzyl 1-(3,4-methylenedioxyphenyl)-2,2,3,3-tetrafluorocyclobutane carboxylate.

The acid prepared in Example 5(a) (0.5 g) was mixed with thionyl chloride (1 ml) and refluxed for 45 minutes. Excess thionylchloride was removed under vacuum. The residue was dissolved in petroleum spirit (b.p. 40°-60°) (5 ml), and added over 5 minutes to a stirred mixture of 3-phenoxybenzylalcohol (0.4 g), pyridine (0.5 ml), benzene (15 ml) and petroleum spirit (b.p. 40°-40°) (15 ml.) After overnight stirring at room temperature the mixture was added to ice water and extracted with diethyl ether. The ether extract was washed with dilute hydrochloric acid, water, sodium bicarbonate solution and dried over anhydrous sodium sulphate. Evaporation of the ether left an oily residue (0.78 g) which was purified by chromatography on silica gel with benzene as eluent to yield 0.7 g of the 3-phenoxy benzyl ester as a clear yellow oil.

Analysis: C 63.54%, H 4.01%, F 15.9%. $C_{25}H_{18}F_4O_5$ requires C 63.30%, H 3.82%, F 16.0%.

EXAMPLES 6 to 20

Using the general method set out in Example 3, the compounds listed in Table 1 were obtained from the appropriate starting materials.

Analysis, spectra and other characterising data were consistent with the stated structures.

Table 1 includes the compounds of Examples 1, 2, 3, 4 and 5 for ease of reference.

TABLE 1

| Example No. | $R^1$ | $R^2$ | $Y^1$ | $Y^2$ | $Y^3$ | $Y^4$ | $Y^5$ | $Y^6$ | $R^3$ |
|---|---|---|---|---|---|---|---|---|---|
| 1 | Cl | H | H | H | H | H | H | H | (a) |
| 2 | $C_2H_5O$ | H | H | H | H | H | H | H | (a) |
| 3 | $C_2H_5O$ | H | F | F | F | F | H | H | (a) |
| 4* | $C_2H_5O$ | H | F | F | F | F | H | H | (a) |
| 5 | —O—CH$_2$—O— | | F | F | F | F | H | H | (a) |
| 6 | $CHF_2CF_2O$ | H | F | F | F | F | H | H | (a) |
| 7 | $C_2H_5O$ | H | F | F | F | F | H | H | (c) |
| 8 | Cl | H | F | F | F | F | H | H | (b) |
| 9 | $C_2H_5O$ | H | F | F | F | F | H | H | (d) |
| 10 | $C_2H_5O$ | H | F | F | F | F | H | H | (b) |
| 11 | Cl | H | F | F | F | F | H | H | (a) |
| 12 | $CH_3O$ | H | F | F | F | F | H | H | (a) |
| 13 | —O—CH$_2$—O— | | F | F | F | F | H | H | (c) |
| 14 | $C_2H_5O$ | H | F | F | F | F | H | H | (f) |
| 15 | Cl | H | F | F | F | F | H | H | (c) |
| 16 | $C_2H_5O$ | H | H | F | F | F | H | H | (c) |
| 17 | $C_2H_5O$ | H | H | F | F | F | H | H | (c) |
| 18 | Cl | H | F | Cl | F | F | H | H | (c) |
| 19 | Cl | H | F | F | F | F | H | H | (e) |
| 20 | $C_2H_5O$ | H | Cl | Cl | F | F | H | H | (c) |

Note*
The compound of Example 4 is the R(−) optical isomer of the compound of Example 3.

EXAMPLE 21

The biological activity of the new cyclobutane esters was examined in a series of tests, the results of which are collected in Table 2.

Insecticidal activity was investigated against the common housefly, *Musca domestica*, and the sheep blowfly, *Lucilia cuprina*. The methods used were as follows:

(i) Housefly

(a) Compound alone

Tests were carried out using a standard DDT-susceptible strain (WHO/IN/1) of *M. domestica*. The compound was applied in an acetone solution by microsyringe to the dorsum of the thorax of two day old female flies reared from pupae of average weight 2.2-2.5 gm/100 pupae. The adult flies were fed on water and sugar-only diet and maintained at 26° C. and 70% RH. The mortalities were counted at 48 hours after treatment and compared with acetone-treated controls. Flies unable to move or stand normally were considered dead. The $LD_{50}$ value was obtained from a logit computer programme based on three replicates of 10 flies at each dose level. The $LD_{50}$ value for DDT determined under the same conditions was 0.26 μg/fly.

(b) Potentiation

The compound can also tested on the insects described above in conjunction with the potentiator "Sesoxane" by pretreating the insect with 1 μg of the potentiator in acetone.

The mortalities were counted at 48 hours after treatment and compared with acetone and acetone/potentiator controls.

The $LD_{50}$ value was determined as described above. For DDT, with the same potentiator the $LD_{50}$ value was 0.24 μg/fly.

About the same levels of potentiation were obtained when "Sesoxane" were replaced by an equal amount of piperonyl butoxide.

(ii) Sheep Blowfly (a) Insecticidal Activity

The compounds were tested for activity against a dieldrin susceptible strain (LBB) which had been collected before dieldrin usage in the field.

The test compound was applied in acetone solution, 0.5 μl dispensed with a Drummond micropipette to the dorsum of the thorax of 2–3 day old females. Adult flies were fed on water and sugar-only and maintained at 25° C. and 60°–70% RH. The mortalities were determined after 24 hours. Moribund flies were regarded as dead. The $LD_{50}$ values, in terms of concentration, were interpolated from a probit/log dose graph using a computer program.

Comparative $LD_{50}$ figures for DDT and dieldrin are 0.17 and 0.25 μg/insect.

(b) Potentiation

Potentiation with "Sesoxane" was investigated as described above in the housefly tests.

TABLE 2

| Compound of Example No. | INSECTICIDAL ACTIVITY | | Repellency Index |
|---|---|---|---|
| | $LD_{50}$ μ/♀ insect | $LD_{50}$ with synergist μ/♀ insect | |
| Sheep Blowfly (*Lucilia cuprina*) | | | |
| 1 | 1.78 | 0.04 | 36 |
| 2 | 0.77 | 0.06 | 61 |
| 3 | 0.05 | 0.001 | 79 |
| 4 | 0.024 | 0.00026 | 73 |
| 5 | 0.04 | 0.003 | 66 |
| 6 | 0.40 | 0.04 | |
| 7 | 0.02 | 0.0004 | 62 |
| 8 | 0.023 | 0.0023 | 77 |
| 9 | 0.11 | 0.03 | 88 |
| 10 | 0.03 | 0.003 | 78 |
| 11 | 0.05 | 0.007 | |
| 12 | | | 17 |
| 13 | 0.03 | 0.001 | 68 |
| 14 | 0.14 | 0.009 | 42 |
| 15 | 0.18 | 0.006 | |
| 16 | 0.10 | 0.001 | |
| 17 | 0.14 | 0.002 | |
| 18 | 0.14 | 0.001 | |
| 19 | 0.028 | 0.002 | |
| 20 | 0.22 | 0.002 | |
| Housefly (*Musca domestica*) | | | |
| 1 | 1.8 | 0.2 | 49 |
| 2 | 1.32 | 0.22 | 81 |
| 3 | 0.13 | 0.003 | 81 |
| 4 | 0.10 | 0.005 | 86 |
| 5 | 0.26 | 0.017 | |
| 6 | 0.6 | 0.036 | 12 |

TABLE 2-continued

| Compound of Example No. | INSECTICIDAL ACTIVITY | | Repellency Index |
|---|---|---|---|
| | $LD_{50}$ μ/♀ insect | $LD_{50}$ with synergist μ/♀ insect | |
| 7 | 0.18 | 0.065 | 89 |
| 8 | 0.55 | 0.01 | |
| 9 | 0.58 | 0.05 | |
| 10 | 0.13 | 0.005 | 84 |
| 11 | 0.34 | 0.018 | |
| 12 | >32 | 0.24 | 18 |
| 13 | 0.12 | 0.018 | 78 |
| 14 | 0.07 | 0.005 | 65 |
| 15 | 0.26 | 0.6 | |
| 16 | | | |
| 17 | | | |
| 18 | | | |
| 19 | | | |
| 20 | | | |

EXAMPLE 22

The following are examples of insecticidal compositions in accordance with the invention. All parts are by weight.

(a) Spray formulation

The following composition is adapted for spray application.

| | |
|---|---|
| Compound of formula I | 4.0 |
| "Sesoxane" or Piperonyl butoxide | 1.0 |
| Deodorized kerosene | 79.4 |
| Alkylated naphthalene | 16.0 |

(b) Aerosol

The following materials are metered into a suitable 'bomb' container sealed and equipped with a valve in the usual way.

| | |
|---|---|
| Compound of formula I | 3.0 |
| Potentiator | 1.0 |
| Methylene chloride | 10.0 |
| 'Freon 12' | 43.0 |
| 'Freon 11' | 43.0 |

(c) Water dispersable power

The following powdered composition is intended for dispersing in water for application as a spray.

| | |
|---|---|
| Compound of formula I | 50.0 |
| Synthetic fine silica | 30.0 |
| Alkyl aryl sodium sulphonate | 1.5 |
| Methyl cellulose (15 cp.) | .25 |
| Attapulgite | 8.25 |

We claim:

1. The (+), (−) and (±) forms of the compounds of the formula I

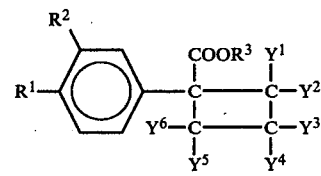

wherein R³ is one of the following groups (a), (b), (d) or (e)

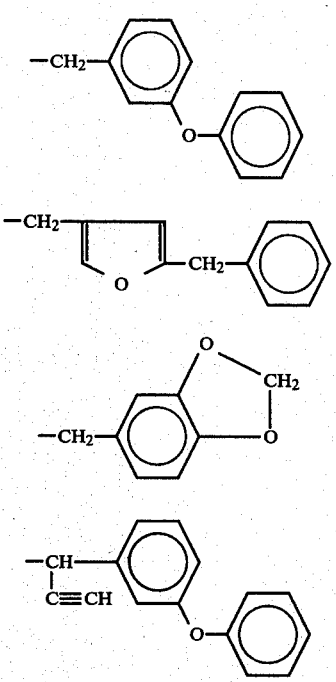

R¹ and R² together represent a methylenedioxy group or if R³ is the group (d) R¹ also represents hydrogen or a methoxy, ethoxy, propoxy, butoxy, tetrafluoroethoxy, methylthio, ethylthio, propylthio, fluoro, chloro, bromo, methyl, ethyl, or nitro group, and R² represents hydrogen or a methyl group; and Y¹, Y², Y³, Y⁴, Y⁵ and Y⁶ are the same or different groups and each is hydrogen or a fluoro, bromo or chloro group, with the proviso that one of Y¹ to Y⁶ is other than hydrogen.

2. Compounds as claimed in claim 1, wherein R¹ is a methoxy, ethoxy or propoxy group and R² is hydrogen, or R¹ and R² together form a methylenedioxy group.

3. Compounds as claimed in claim 1, wherein R³ is one of the groups (a), and (e) as defined in claim 1.

4. Compounds as claimed in claim 1, wherein from one to all six of the groups Y¹ to Y⁶ is a fluoro group, the remainder (if any) being hydrogen.

5. Compounds as claimed in claim 4, wherein Y¹, Y², Y³ and Y⁴ are all fluoro and Y⁵ and Y⁶ are hydrogen.

6. The (+), (−) and (±) forms of 3'-phenoxybenzyl 1-(3,4-methylenedioxyphenyl)-2,2,3,3-tetrafluorocyclobutane-carboxylate.

7. The (+), (−) and (±) forms of α-ethynyl-3'-phenoxybenzyl 1-(3,4-methylenedioxyphenyl)-2,2,3,3-tetrafluorocyclobutane-carboxylate.

8. Insecticidal compositions comprising an insecticidally effective amount of one or more of the compounds of formula I, as stated in claim 1, where R³ is one of the groups (a), (b), (d) and (e), incorporated in a suitable inert liquid or solid carrier.

9. Insecticidal compositions as claimed in claim 8, additionally containing at least one synergistic or potentiating agent which is a pyrethrin synergist.

10. Insecticidal compositions as claimed in claim 8 additionally containing at least one synergistic or potentiating agent selected from the group consisting of α-[2-(2-butoxyethoxy)ethoxy]-4,5-methylenedioxy-2-propyltoluene; 3-hexyl-5(3,4-methylenedioxyphenyl)-2-cyclohexanone; 2-(3,4-methylenedioxy-phenoxy)-3,6,9-trioxaundecane; 1,2-(methylenedioxy)-4-[2-(octylsulfinyl)propyl]-benzene; and dipropyl-5,6,7,8-tetrahydro-7-methylnaphtho-[2,3,d]-1,3-dioxole-5,6-dicarboxylate.

11. Insectidical compositions as claimed in claim 10, wherein the synergist is 2-(3,4-methylenedioxy-phenoxy)-3,6,9-trioxaundecane or α-[2-(2-butoxyethoxy)ethoxy]-4,5-methylenedioxy-2-propyltoluene used in an amount from 1/1000th to 5 times the weight of the compound I.

12. Insecticidal compositions as claimed in claim 10, wherein the amount of 2-(3,4-methylenedioxy-phenoxy)-3,6,9-trioxaundecane or α-[2-(2-butoxyethoxy)ethoxy]-4,5-methylenedioxy-2-propyltoluene used is from about 1/100th to an equal part by weight per part of the compound I.

* * * * *